US012773686B2

(12) United States Patent
Giiazov et al.

(10) Patent No.: US 12,773,686 B2
(45) Date of Patent: Oct. 27, 2026

(54) DEHYDRATION CATALYSTS FOR ACROLEIN PRODUCTION FROM GLYCEROL AND METHODS FOR FORMING THE SAME

(71) Applicant: Trillium Renewable Chemicals, Knoxville, TN (US)

(72) Inventors: Oleg Giiazov, New York, NY (US); Dennis Jewell, Dale, TX (US); Anthony Martinez, Nashville, TN (US); Corey Tyree, Knoxville, TN (US); Chance Hostetler, Golden, CO (US)

(73) Assignee: Trillium Renewable Chemicals, Knoxville, TN (US)

( * ) Notice: Subject to any disclaimer, the term of this patent is extended or adjusted under 35 U.S.C. 154(b) by 0 days.

(21) Appl. No.: 19/530,963

(22) Filed: Feb. 5, 2026

(65) Prior Publication Data

US 2026/0166525 A1 Jun. 18, 2026

Related U.S. Application Data

(63) Continuation of application No. 19/395,089, filed on Nov. 20, 2025.

(Continued)

(51) Int. Cl.
*B01J 21/06* (2006.01)
*B01J 23/652* (2006.01)

(Continued)

(52) U.S. Cl.
CPC ......... *B01J 23/6527* (2013.01); *B01J 21/066* (2013.01); *B01J 37/12* (2013.01);

(Continued)

(58) Field of Classification Search
None
See application file for complete search history.

(56) References Cited

U.S. PATENT DOCUMENTS 7,396,962 B1 7/2008 Dubois et al.
7,494,953 B2 2/2009 Houzvicka et al.

(Continued)

FOREIGN PATENT DOCUMENTS

WO WO-2021211466 A1 * 10/2021 .............. B01J 35/37
WO 2023105430 A1 6/2023

OTHER PUBLICATIONS

International Search Report and Written Opinion dated Feb. 26, 2026, pertaining to Int'l Patent Application No. PCT/US2025/056801, 19 pgs.

(Continued)

*Primary Examiner* — Daniel Berns
(74) *Attorney, Agent, or Firm* — Dinsmore & Shohl LLP

(57) ABSTRACT

A method for forming a dehydration catalyst may comprise peptizing a catalyst precursor with an acid, a cellulose ether, or both, thereby forming a catalyst precursor sol, wherein the catalyst precursor comprising a tungstated support of tungsten and at least one of zirconium oxides, zirconium hydroxides, or titanium oxides; subjecting the catalyst precursor sol to kneading and extrusion to form one or more catalyst precursor extrudates; calcining the one or more catalyst precursor extrudates to form a calcined catalyst precursor; and cooling the calcined catalyst precursor to form the dehydration catalyst.

19 Claims, 1 Drawing Sheet

Related U.S. Application Data

(60) Provisional application No. 63/724,991, filed on Nov. 26, 2024.

(51) Int. Cl.
*B01J 37/12* (2006.01)
*C07C 51/25* (2006.01)
*C07C 253/26* (2006.01)

(52) U.S. Cl.
CPC .......... *C07C 51/252* (2013.01); *C07C 253/26* (2013.01); *C07C 2521/06* (2013.01); *C07C 2523/652* (2013.01)

(56) References Cited

U.S. PATENT DOCUMENTS

| | | | |
|---|---|---|---|
| 7,531,699 | B2 | 5/2009 | Dubois |
| 7,655,818 | B2 | 2/2010 | Dubois et al. |
| 9,162,954 | B2 | 10/2015 | Magatani et al. |
| 9,205,403 | B2 | 12/2015 | Dubois |
| 9,321,040 | B2 | 4/2016 | Joe et al. |
| 9,527,065 | B2 | 12/2016 | Kim et al. |
| 9,708,249 | B1 | 7/2017 | Goyal et al. |
| 9,738,582 | B2 | 8/2017 | Dubois |
| 9,914,699 | B2 | 3/2018 | Dubois et al. |
| 2010/0048850 | A1 | 2/2010 | Dubois |

OTHER PUBLICATIONS

Liebig et al. “Glycerol conversion to acrylonitrile by consecutive dehydration over WO3/TiO2 and ammoxidation over Sb-(Fe, V)-O”, Applied Catalysis B: Environmental 132-133 (2013) 170-182.

* cited by examiner

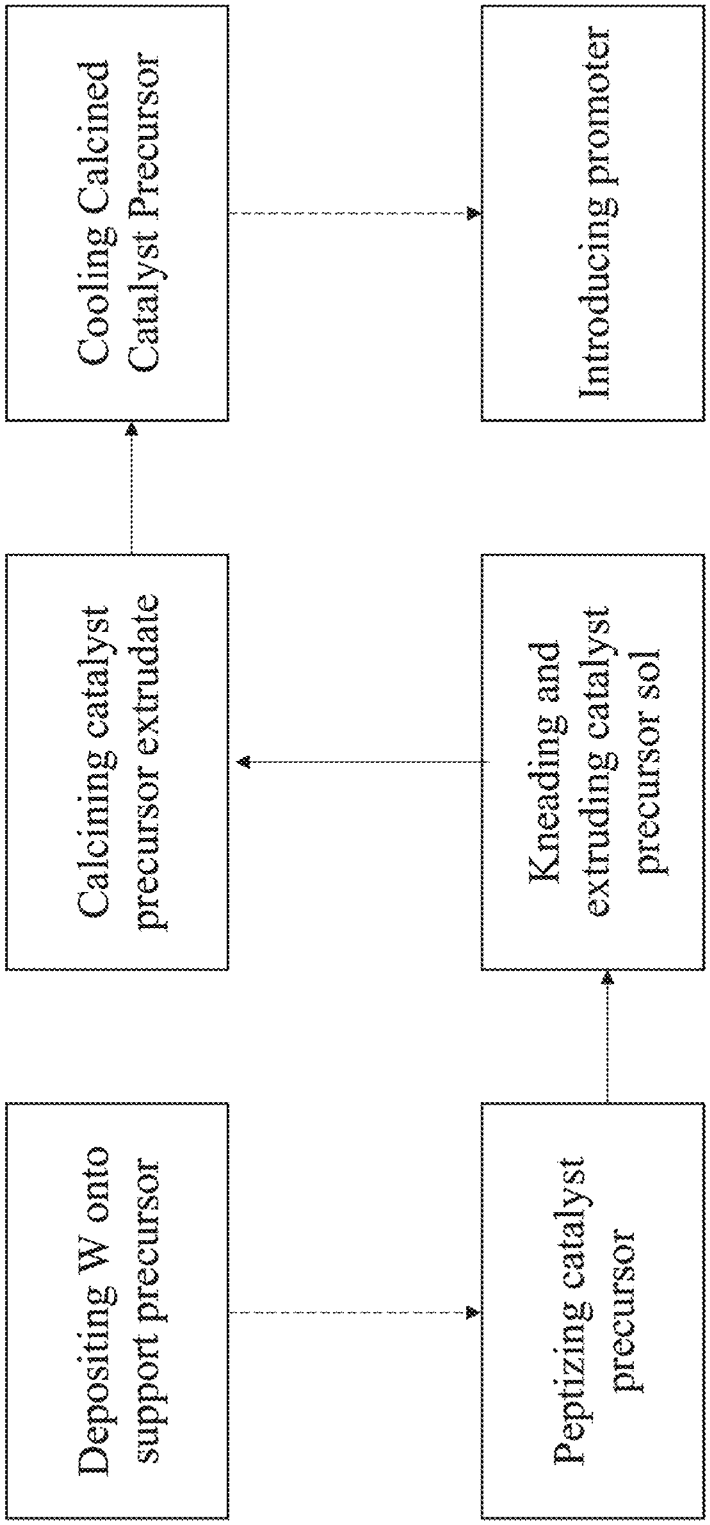
Depositing W onto support precursor
Peptizing catalyst precursor
Kneading and extruding catalyst precursor sol
Calcining catalyst precursor extrudate
Cooling Calcined Catalyst Precursor
Introducing promoter

DEHYDRATION CATALYSTS FOR ACROLEIN PRODUCTION FROM GLYCEROL AND METHODS FOR FORMING THE SAME

CROSS REFERENCE TO RELATED APPLICATIONS

This application is a continuation of the U.S. patent application Ser. No. 19/395,089 (TUW0002PA) filed Nov. 20, 2025, which claims the benefit of U.S. Provisional Application Ser. No. 63/724,991 (TUW0002MA), filed Nov. 26, 2024, which is hereby incorporated by reference.

FIELD

The present disclosure relates to the field of acrolein and acrylonitrile production, and particularly to production of acrolein from glycerol. More particularly, it relates to dehydration catalysts for the same, as well as methods for forming the catalysts.

BACKGROUND

Acrylonitrile (ACN) is a man-made organic compound with the formula $CH_2$═CH—CN. Acrylonitrile is used as a monomer in the production of the homopolymer polyacrylonitrile, as well as for producing copolymers including but not limited to styrene-acrylonitrile (SAN) acrylonitrile butadiene styrene (ABS), acrylonitrile, 10 styrene acrylate (ASA), and other synthetic rubbers such as acrylonitrile butadiene (NBR). Acrylonitrile may further be used as an intermediate in the production of nylon and acrylamide, and as a precursor in carbon fiber.

SUMMARY

Most Acrylonitrile is produced by the so-called SOHIO (Standard Oil of Ohio) process, by means of gas phase ammoxidation (ammonia and oxygen) of propylene. However, the worldwide shift away from fossil fuels to green energy has also impacted acrylonitrile processes, such that 'green' and renewable feedstocks for acrylonitrile are now desired. One such feedstock of study is glycerol (1,2,3-propanetriol; glycerine), a significant by-product in biodiesel production.

In the glycerol to acrylonitrile process, glycerol may be catalytically dehydrated to acrolein, which is subsequently subjected to a catalytic ammoxidation step to from acrylonitrile. Accordingly, improved dehydration and ammoxidation catalysts to selectively convert glycerol to acrolein and acrolein to acrylonitrile are continually desired.

Accordingly, embodiments herein fulfill the aforementioned need by providing dehydration catalysts that exhibit improved levels of thermal stability, pore size distribution, deactivation rates, regeneration ability, or combinations thereof as compared to comparable dehydration catalysts, which may be evidenced by the subsequent conversion of glycerol to acrolein with reduced levels of undesired by-products. Without being limited by theory, these improvements may be sourced from a variety of factors, including but not limited to selecting particular catalyst support, acid site, and/or promoter combinations as well as detailed control of the calcination heating and cooling temperature ramps in forming the catalyst.

According to one embodiment herein, a method for forming a dehydration catalyst comprises peptizing a catalyst precursor with an acid, a cellulose ether, or both, thereby forming a catalyst precursor sol, wherein the catalyst precursor comprising a tungstated support of tungsten and at least one of zirconium oxides, zirconium hydroxides, or titanium oxides; subjecting the catalyst precursor sol to kneading and extrusion to form one or more catalyst precursor extrudates; calcining the one or more catalyst precursor extrudates to form a calcined catalyst precursor; and cooling the calcined catalyst precursor to form the dehydration catalyst.

According to another embodiment herein, a method of producing acrolein comprising introducing a feed stream comprising glycerol into one or more dehydration reactors comprising a dehydration catalyst, thereby dehydrating the glycerol into acrolein, wherein the dehydration catalyst comprises a tungstated support comprising platinum acid sites, palladium acid sites, or both on a surface of the support; the support comprises zirconium oxide, zirconium hydroxide, titanium oxide, or combinations thereof; the dehydration catalyst comprises from 5 wt. % to 25 wt. % tungstate; and the dehydration catalyst comprises from 0.1 wt. % to 4 wt. % platinum, from 0.1 wt. % to 4 wt. % palladium, or a combined 0.1 wt. % to 4 wt. % platinum and palladium.

Additional features and advantages of the described embodiments will be set forth in the detailed description which follows, and in part will be readily apparent to those skilled in the art from that description or recognized by practicing the described embodiments, including the detailed description which follows as well as the claims.

BRIEF DESCRIPTION OF THE DRAWINGS

The following detailed description of specific embodiments of the present disclosure can be best understood when read in conjunction with the following drawings, where like structure is indicated with like reference numerals and in which:

FIG. 1 illustrates a process flow diagram for a method for forming a dehydration catalyst, according to embodiments herein.

Reference will now be made in greater detail to various embodiments, some embodiments of which are illustrated in the accompanying drawings.

DETAILED DESCRIPTION

As previously stated, embodiments described herein generally relate to acrolein and acrylonitrile production, and particularly to production of acrolein from glycerol. More particularly, embodiments herein relates to dehydration catalysts for the same, as well as methods for forming the catalysts.

As previously stated, at least some of the embodiments herein may be directed to a dehydration catalyst. The dehydration catalyst may generally comprise a support and one or more acid sites on the support, i.e. a coordinatively unsaturated metal cation on the surface of the support. For example, and in embodiments, the support may comprise zirconium oxide, zirconium hydroxide, titanium oxide, or combinations thereof. The acid sites may comprise tungsten, such that the support may be regarded as a tungstated support and/or the catalyst may comprise a complex of tungstate and at least one of the zirconium oxide, zirconium hydroxide, and titanium oxide.

In embodiments, the tungstate may be present in the dehydration catalyst in an amount of from 5 wt. % to 25 wt.

% by weight of the dehydration catalyst, such as from 5 to 6 wt. %, from 6 to 8 wt. %, from 8 to 10 wt. %, from 10 to 15 wt. %, from 15 to 20 wt. %, from 20 to 23 wt. %, from 23 to 24 wt. %, from 24 to 25 wt. %, or any combinations of the previous ranges or smaller range therein, such as from 10 to 20 wt. % by weight of the dehydration catalyst. Accordingly, the support may be the balance of the weight of the dehydration catalyst, such as in an amount of from 95 wt. % to 75 wt. % in at least some embodiments, or the balance amount as appropriate given any remaining additives to the dehydration catalyst, such as but not limited to the catalyst promoters described in further detail below.

The dehydration catalyst may also comprise one or more catalyst promoters. For example, the dehydration catalyst may comprise an electronic promoter, such as, but not limited to platinum, palladium, cobalt, nickel, rhenium, zinc, copper, chromium, molybdenum, sodium, potassium, rubidium, cesium or combinations thereof. In embodiments, the catalyst may comprise from 0.1 wt. % to 10 wt. % promoter by weight of the dehydration catalyst, such as from 0.1 to 0.5 wt. %, from 0.5 to 1 wt. %, from 1 to 2 wt. %, from 2 to 3 wt. %, from 3 to 4 wt. %, from 4 to 5 wt. %, from 5 to 8 wt. %, from 8 to 10 wt. %, or any combination of the previous ranges or smaller range therein, such as from 0.1 wt. % to 4 wt. % promoter, by weight of the dehydration catalyst.

Additionally or alternatively, the dehydration catalyst may comprise another catalyst promoter, such as but not limited to iron, gallium, tin, manganese, magnesium, calcium, strontium, barium or combinations thereof. In embodiments, the catalyst may comprise from 0.1 wt. % to 10 wt. % of the another catalyst promoter by weight of the dehydration catalyst, such as from 0.1 to 0.5 wt. %, from 0.5 to 1 wt. %, from 1 to 2 wt. % from 2 to 3 wt. %, from 3 to 4 wt. %, from 4 to 5 wt. %, from 5 to 6 wt. %, from 6 to 8 wt. %, from 8 to 10 wt. %, or combinations of the previous or smaller ranges therein, such as from 0.5 wt. % to 6 wt. %.

In embodiments, the dehydration catalyst may have a mesoporous pore structure.

As previously stated, embodiments herein may also comprise methods of forming a dehydration catalyst, such as any of the dehydration catalysts hereinbefore described. For example, and now referring to FIG. 1, the method may initially comprise forming a catalyst precursor by depositing tungsten onto a catalyst support, such as any of the catalyst supports previously mentioned. In embodiments, the tungsten that is or has been deposited on the catalyst support may be in the form of a tungstate. In embodiments, the deposition of the tungsten may occur according to impregnation, although this is not required.

Still referring to FIG. 1, the method may then comprise peptizing the catalyst precursor with an acid, a cellulose ether, or both thereby forming a catalyst precursor sol. In embodiments, the acid may be added to the catalyst precursor, before, after, or concurrently with the cellulose ether. The acid may comprise an inorganic acid (such as but not limited to nitric acid) or an organic acid (such as but not limited to a carboxylic acid, citric acid, acetic acid, or combinations thereof). In at least some embodiments, the acid may comprise oxalic acid. The cellulose ether may be any cellulose ether that is regarded as water soluble, such as, but not limited to carboxymethyl cellulose, hydroxypropyl cellulose, ethyl cellulose carboxyethyl cellulose, methylethyl cellulose, methyl cellulose, hydroxyethyl cellulose, propyl cellulose, carboxymethyl hydroxyethyl cellulose, methyl hydroxypropyl cellulose, hydroxypropylmethyl cellulose, ethyl carboxymethyl cellulose, or combinations thereof.

In embodiments, a ratio of acid to cellulose ether (if both are present) in the peptizing step, i.e., in the peptizing solution, may be a majority acid and a balance cellulose ether, such as from 50.01 vol. % acid to 80 vol. % % acid by volume of the peptizing solution, such as from 50.01 to 51 vol. %, from 51 to 55 vol. %, from 55 to 58 vol. %, from 58 to 60 vol. %, from 60 to 62 vol. %, from 62 to 70 vol. %, from 70 to 80 vol. %, or any combination of the previous ranges or smaller range therein, such as from 58 vol. % to 62 vol. % acid and the balance cellulose ether.

The catalyst precursor sol may then be subjected to kneading and extrusion to form one or more catalyst precursor extrudates. The catalyst precursor extrudates may then be calcined to form a calcined catalyst precursor. Without being limited by theory, both the peak calcination temperature and the temperature ramp to the peak calcination temperature may impact subsequent catalyst stability and support. Accordingly, in at least some embodiments, the peak calcination temperature of the calcination step may be from 500° C. to 1000° C., such as from 500° C. to 510° C., from 510° C. to 520° C., from 520° C. to 550° C., from 550° C. to 600° C., from 600° C. to 650° C., from 650° C. to 700° C., from 700° C. to 720° C., from 720° C. to 750° C., from 750° C. to 800° C., from 800° C. to 850° C., from 850° C. to 900° C., from 900° C. to 950° C., from 950° C. to 1000° C., or any combinations of the previous ranges or small ranges therein, such as from 510° C. to 720° C. Further, the calcining of the one or more catalyst precursor extrudates may occur at a temperature ramp of from 1° C. per minute to 10° C. per minute for a period of from 10 minutes to 6 hours to result in the desired dehydration catalyst properties.

Further, without being limited by theory, it is contemplated that the rate of cooling of the calcined catalyst precursor may impact subsequent catalyst stability and performance. Accordingly, cooling the calcined catalyst precursor may occur in a multi-stage procedure comprising a first cooling ramp, a second cooling ramp, and a third cooling ramp. The first cooling ramp may be from 3° C. per minute to 180° C. per minute from a calcined catalyst precursor temperature of from 1000° C. to 310° C. The second cooling ramp may be from 1° C. per minute to 60° C. per minute from a calcined catalyst precursor temperature of from 310° C. to 120° C. The third cooling ramp may be from 0.3° C. per minute to 30° C. per minute from a calcined catalyst precursor temperature of from 120° C. to 20° C. In other words, the third cooling ramp may be slower than the second cooling ramp, which may in turn be cooler than the first cooling ramp.

In at least some embodiments, it may be desired to give the dehydration catalyst additional functionalities, or to reinforce the structure of the dehydration catalyst. Accordingly, the method of making the catalyst may further comprise introducing the promoters previously described. Without being limited by theory, it is contemplated that adding iron to the dehydration catalyst may have unexpected benefits to the thermal stability and/or performance of the catalyst.

In embodiments, the catalyst promoter may be introduced as a salt selected from one or more of nitrates, chlorides, sulfates, or oxalates. Alternatively, the promoter may be introduced as one or more of hydroxides, carbonates, or bicarbonates.

As previously stated, embodiments herein may also comprise methods of producing acrolein from glycerol utilizing a dehydration catalyst, such as any of the dehydration catalysts previously mentioned or formed according to the methods previously mentioned. The method may comprise introducing a feed stream comprising glycerol into one or more reactors comprising the dehydration catalyst, thereby dehydrating the glycerol into acrolein. In embodiments, the feed stream may further comprise acetol.

In at least some embodiments, the method may further comprising introducing the acrolein, oxygen, and ammonia to one or more ammoxidation reactors comprising an ammoxidation catalyst, thereby converting the acrolein to acrylonitrile. The ammoxidation catalyst may comprise oxides of molybdenum, bismuth, iron, antimony, tin, vanadium, tungsten, antimony, zirconium, titanium, chromium, nickel, aluminum, phosphorus, gallium, or combinations thereof.

In at least some embodiments, the method may further comprise regenerating the dehydration catalyst, the ammoxidation catalyst, or both, using an oxygen-containing gas stream, a hydrogen-containing gas stream, or both.

In at least one embodiment herein, a method of producing acrolein may comprise introducing a feed stream comprising glycerol into one or more dehydration reactors comprising a dehydration catalyst, thereby dehydrating the glycerol into acrolein, wherein the dehydration catalyst comprises a tungstated support comprising platinum acid sites, palladium acid sites, or both on a surface of the support.

EXAMPLES

Example 1

A tungstated zirconium hydroxide catalyst precursor (supplied by Luxfer MEL Technologies) was used as the catalyst support. The catalyst precursor had 14.8 wt. % $WO_3$ content, calculated based on calcined material. A 4% nitric acid solution was used as the peptizing agent. The peptizing solution was added to the tungstated zirconium hydroxide catalyst support, followed by homogenization of said molding mass.

After reaching optimal moldable properties, the mixture was extruded, and the extrudates were dried with the following protocol: 50° C. for 2 hours with 70% humidity, 110° C. for 2 hours with 40% humidity, and 130° C. for 3 hours with 20% humidity. Calcination of the extrudates was performed in an oven in static air flow with the peak calcination temperature of 900° C. for 4 hours. The heating ramp for the catalyst extrudates was 2° C. per minute.

The cooling of the calcined catalyst was performed in a single ramp of 3C per minute down to 100° C. Subsequently, the calcined support was impregnated with chloroplatinic acid to introduce 0.56 wt. % platinum utilizing the incipient-wetness technique. The impregnated catalyst support was then dried before subsequent calcining in dry air flow at 500° C. for 2 hours, resulting in the final dehydration catalyst according to embodiments herein.

Example 2

The dehydration catalyst of Example 2 was prepared according to Example 1, except the catalyst was impregnated by the incipient-wetness technique with tetraamineplatinum(II) nitrate to introduce 1.02 wt. % platinum.

Example 3

The dehydration catalyst of Example 3 was prepared according to Example 1, except the catalyst was impregnated by the incipient-wetness technique with Palladium(II) nitrate to introduce 1.05 wt. % palladium.

Examples 1-3 were evaluated for glycerol dehydration in a pilot-scale fixed-bed reactor loaded with 50 g of the respective catalyst and run at either 310° C. or 280° C. with WHSV=2 $h^{-1}$, and pressure of 0.2-0.6 bar g. Feed was 20 wt. % glycerol and 80 wt. % bi-distilled water. Glycerol conversion and selectivity of acrolein, propanal, and ethanal after 4 hours and 12 hours on stream are shown below in Table 1.

TABLE 1

Glycerol Conversion and Selectivity of Examples 1-3

| | | | | Selectivity, % | | | | | |
|---|---|---|---|---|---|---|---|---|---|
| | Temp | Conversion, % Glycerol | | Acrolein | | Propanal ($C_3H_6O$) | | Ethanal ($CH_3CHO$) | |
| Example | (° C.) | 4 hr | 12 hr | 4 hr | 12 hr | 4 hr | 12 hr | 4 hr | 12 hr |
| 1 | 310 | 99.58 | 98.43 | 72.4 | 80.85 | 4.49 | 1.89 | 8.34 | 4.05 |
| 2 | 280 | 99.31 | 97.28 | 85.13 | 86.48 | 1.56 | 0.9 | 1.37 | 0.89 |
| 3 | 280 | 99.13 | 97.83 | 84.36 | 83.75 | 1.57 | 1.26 | 2.16 | 1.72 |

As shown in Table 1 above, each of the Examples exhibited high conversion rates of glycerol as well as high selectivity to acrolein over propanal and ethanal.

The present disclosure may include one or more aspects. A first aspect may include a method for forming a dehydration catalyst, comprising: peptizing a catalyst precursor with an acid, a cellulose ether, or both, thereby forming a catalyst precursor sol, wherein the catalyst precursor comprising a tungstated support of tungsten and at least one of zirconium oxides, zirconium hydroxides, or titanium oxides; subjecting the catalyst precursor sol to kneading and extrusion to form one or more catalyst precursor extrudates; calcining the one or more catalyst precursor extrudates to form a calcined catalyst precursor; and cooling the calcined catalyst precursor to form the dehydration catalyst.

A second aspect may include the first aspect, and may further comprise forming the catalyst precursor by depositing tungsten onto at least one of zirconium oxides, zirconium hydroxides, or titanium oxides dispersed in an aqueous medium.

A third aspect may include any previous aspect, wherein the acid comprises an organic acid comprising oxalic acid, citric acid, acetic acid, or combinations thereof.

A fourth aspect may include any previous aspect, wherein the cellulose ether comprises carboxymethyl cellulose, hydroxypropyl cellulose, ethyl cellulose carboxyethyl cellulose, methylethyl cellulose, methyl cellulose, hydroxyethyl cellulose, propyl cellulose, carboxymethyl hydroxyethyl cellulose, methyl hydroxypropyl cellulose, hydroxypropylmethyl cellulose, ethyl carboxymethyl cellulose, or combinations thereof.

A fifth aspect may include any previous aspect, wherein cooling the calcined catalyst precursor occurs in a multi-stage procedure comprising: a first cooling ramp of from 3° C. per minute to 180° C. per minute from a calcined catalyst precursor temperature of from 1000° C. to 310° C.; a second cooling ramp of from 1° C. per minute to 60° C. per minute from a calcined catalyst precursor temperature of from 310° C. to 120° C.; and a third cooling ramp of from 0.3° C. per minute to 30° C. per minute from a calcined catalyst precursor temperature of from 120° C. to 20° C.

A sixth aspect may include any previous aspect, wherein the peak calcination temperature is from 500° C. to 1000° C.; and calcining the extruded catalyst support precursor occurs at a temperature ramp of from 1° C. per minute to 10° C. per minute for a period of from 10 minutes to 6 hours.

A seventh aspect may include any previous aspect, wherein the organic acid comprises oxalic acid.

A eighth aspect may include any previous aspect, and may further comprise introducing a catalyst promoter to the dehydration catalyst.

A ninth aspect may include the eighth aspect, wherein the dehydration catalyst comprises from 0.05 wt. % to 10 wt. % catalyst promoter.

A tenth aspect may include the eighth aspect, wherein the catalyst promoter is selected from one or more of the group consisting of iron, gallium, tin, manganese, magnesium, calcium, strontium, or barium.

An eleventh aspect may include the tenth aspect, wherein the dehydration catalyst comprises from 0.5 wt. % to 6 wt. % iron oxide.

A twelfth aspect may include the tenth aspect, wherein the catalyst promoter is introduced as a salt selected from one or more of hydroxides, carbonates, bicarbonates, nitrates, chlorides, sulfates, or oxalates.

A thirteenth aspect may include any of the eighth through eleventh aspects, wherein the catalyst promoter is selected from one or more of platinum, palladium, nickel, cobalt, zinc, copper, chromium, molybdenum, rhenium, sodium, potassium, rubidium, or cesium.

A fourteenth aspect may include the thirteenth aspect, wherein the promoter is introduced as a salt selected from one or more of the group consisting of hydroxides, carbonates, bicarbonates, nitrates, chlorides, sulfates, or oxalates.

A fifteenth aspect may include the fourteenth aspect, wherein the dehydration catalyst comprises from 0.1 wt. % to 4 wt. % platinum, from 0.1 wt. % to 4 wt. % palladium, or a combined 0.1 wt. % to 4 wt. % platinum and palladium.

A sixteenth aspect may include any previous aspect, wherein the dehydration catalyst comprises from 5 wt. % to 25 wt. % tungstate.

A seventeenth aspect may include any previous aspect, and may further comprise a method of producing acrolein comprising introducing a feed stream comprising glycerol into one or more dehydration reactors comprising the dehydration catalyst, thereby dehydrating the glycerol into acrolein.

An eighteenth aspect may include the seventeenth aspect, and may further comprise introducing the acrolein, oxygen, and ammonia to one or more ammoxidation reactors comprising an ammoxidation catalyst, thereby converting the acrolein to acrylonitrile.

A nineteenth aspect may include either the seventeenth or eighteenth aspects, wherein the feed stream further comprises acetol.

A twentieth aspect may include a method of producing acrolein comprising introducing a feed stream comprising glycerol into one or more dehydration reactors comprising a dehydration catalyst, thereby dehydrating the glycerol into acrolein, wherein: the dehydration catalyst comprises a tungstated support comprising platinum acid sites, palladium acid sites, or both on a surface of the support; the support comprises zirconium oxide, zirconium hydroxide, titanium oxide, or combinations thereof, the dehydration catalyst comprises from 5 wt. % to 25 wt. % tungstate; and the dehydration catalyst comprises from 0.1 wt. % to 4 wt. % platinum, from 0.1 wt. % to 4 wt. % palladium, or a combined 0.1 wt. % to 4 wt. % platinum and palladium.

A twenty-first aspect may include the twentieth aspect, and may further comprise introducing the acrolein, oxygen, and ammonia to one or more ammoxidation reactors comprising an ammoxidation catalyst, thereby converting the acrolein to acrylonitrile.

It is also noted that recitations herein of “at least one” component, element, etc., should not be used to create an inference that the alternative use of the articles “a” or “an” should be limited to a single component, element, etc. The singular forms “a,” “an” and “the” include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned.

It is noted that one or more of the following claims utilize the term “wherein” as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term “comprising.” It is noted that the use of the terms “having” or “including”, or grammatical variations thereof, in this disclosure should also be interpreted in like manner as the more commonly used open-ended preamble term “comprising”.

As used in this disclosure, terms such as “first” and “second” are arbitrarily assigned and are merely intended to differentiate between two or more instances or components. It is to be understood that the words “first” and “second” serve no other purpose and are not part of the name or description of the component, nor do they necessarily define a relative location, position, or order of the component. Furthermore, it is to be understood that the mere use of the term “first” and “second” does not require that there be any “third” component, although that possibility is contemplated under the scope of the present disclosure.

It is noted that terms like “preferably,” “commonly,” and “typically,” when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

Having described the subject matter of the present embodiments herein in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present embodiments including, but not limited to, embodiments defined in the appended claims. More specifically, although some aspects of the present embodiments are identified herein as preferred or particularly advantageous, it is contemplated that the present embodiments is not necessarily limited to these aspects.

The invention claimed is:

1. A method for forming a dehydration catalyst, comprising:

peptizing a catalyst precursor with an acid, a cellulose ether, or both, thereby forming a catalyst precursor sol, wherein the catalyst precursor comprises a tungstated support of tungsten and at least one of zirconium oxides, zirconium hydroxides, or titanium oxides;

subjecting the catalyst precursor sol to kneading and extrusion to form one or more catalyst precursor extrudates;

calcining the one or more catalyst precursor extrudates to form a calcined catalyst precursor; and cooling the calcined catalyst precursor to form the dehydration catalyst, wherein:

the dehydration catalyst comprises from 91 wt. % to 100 wt. % tungstate and at least one of zirconium oxide, zirconium hydroxide, or titanium oxide, combined, by total weight of the dehydration catalyst.

2. The method of claim 1, wherein the dehydration catalyst comprises from 95 wt. % to 100 wt. % tungstate and at least one of zirconium oxide, zirconium hydroxide, or titanium oxide, combined, by total weight of the dehydration catalyst.

3. The method of claim 1, further comprising introducing a catalyst promoter to the dehydration catalyst, thereby forming a promoted dehydration catalyst, wherein:

the catalyst promoter is selected from:

one or more of the group consisting of platinum, palladium, nickel, cobalt, zinc, copper, chromium, molybdenum, rhenium, sodium, potassium, rubidium, or cesium, one or more of the group consisting of iron, gallium, tin, manganese, magnesium, calcium, strontium, or barium, or both, and the promoted dehydration catalyst comprises from 95 wt. % to 100 wt. % catalyst promoter, tungstate, and at least one of zirconium oxide, zirconium hydroxide, or titanium oxide, combined, by total weight of the promoted dehydration catalyst.

4. The method of claim 1, further comprising forming the catalyst precursor by depositing tungsten onto at least one of zirconium oxides, zirconium hydroxides, or titanium oxides dispersed in an aqueous medium.

5. The method of claim 1, wherein the acid comprises an organic acid comprising oxalic acid, citric acid, acetic acid, or combinations thereof.

6. The method of claim 1, wherein the cellulose ether comprises carboxymethyl cellulose, hydroxypropyl cellulose, ethyl cellulose carboxyethyl cellulose, methylethyl cellulose, methyl cellulose, hydroxyethyl cellulose, propyl cellulose, carboxymethyl hydroxyethyl cellulose, methyl hydroxypropyl cellulose, hydroxypropylmethyl cellulose, ethyl carboxymethyl cellulose, or combinations thereof.

7. The method of claim 1, wherein cooling the calcined catalyst precursor occurs in a multi-stage procedure comprising:

a first cooling ramp of from 3° C. per minute to 180° C. per minute from a calcined catalyst precursor temperature of from 1000° C. to 310° C.;

a second cooling ramp of from 1° C. per minute to 60° C. per minute from a calcined catalyst precursor temperature of from 310° C. to 120° C.; and a third cooling ramp of from 0.3° C. per minute to 30° C. per minute from a calcined catalyst precursor temperature of from 120° C. to 20° C.

8. The method of claim 1, wherein:

a peak calcination temperature in the calcining the one or more catalyst precursor extrudates step is from 500° C. to 1000° C.; and calcining the one or more catalyst precursor extrudates occurs at a temperature ramp of from 1° C. per minute to 10° C. per minute for a period of from 10 minutes to 6 hours.

9. The method of claim 1, wherein the acid comprises oxalic acid.

10. The method of claim 1, further comprising introducing a catalyst promoter to the dehydration catalyst, thereby forming a promoted dehydration catalyst.

11. The method of claim 10, wherein the catalyst promoter is selected from one or more of the group consisting of platinum, palladium, nickel, cobalt, zinc, copper, chromium, molybdenum, rhenium, sodium, potassium, rubidium, or cesium.

12. The method of claim 11, wherein the dehydration catalyst comprises from 0.1 wt. % to 4 wt. % platinum, from 0.1 wt. % to 4 wt. % palladium, or a combined 0.1 wt. % to 4 wt. % platinum and palladium.

13. The method of claim 10, wherein the dehydration catalyst comprises from 0.05 wt. % to 10 wt. % catalyst promoter.

14. The method of claim 10, wherein the catalyst promoter is selected from one or more of the group consisting of iron, gallium, tin, manganese, magnesium, calcium, strontium, or barium.

15. The method of claim 14, wherein:

the catalyst promoter is iron; and the dehydration catalyst comprises from 0.5 wt. % to 6 wt. % iron oxide.

16. The method of claim 14, wherein the catalyst promoter is introduced as a salt selected from one or more of hydroxides, carbonates, bicarbonates, nitrates, chlorides, sulfates, or oxalates.

17. The method of claim 1, wherein the dehydration catalyst comprises from 5 wt. % to 25 wt. % tungstate.

18. A method of producing acrolein utilizing the dehydration catalyst formed according to claim 1, comprising introducing a feed stream comprising glycerol into one or more dehydration reactors comprising the dehydration catalyst, thereby dehydrating the glycerol into acrolein.

19. The method of claim 18, further comprising introducing oxygen, ammonia, and the acrolein to one or more ammoxidation reactors comprising an ammoxidation catalyst, thereby converting the acrolein to acrylonitrile.

* * * * *